United States Patent [19]

Kent

[11] 4,274,983
[45] Jun. 23, 1981

[54] POLYMERIC CASTS

[75] Inventor: Eric G. Kent, Sarnia, Canada

[73] Assignee: Polysar Limited, Sarnia, Canada

[21] Appl. No.: 9,287

[22] Filed: Feb. 5, 1979

[30] Foreign Application Priority Data

Feb. 17, 1978 [CA] Canada ................................. 297189

[51] Int. Cl.$^3$ ............................................. C08L 7/00
[52] U.S. Cl. .................................... 260/4 R; 128/90; 260/42.47
[58] Field of Search .............. 128/90; 260/4 R, 42.47, 260/887, 889, 897 B; 525/186

[56] References Cited

U.S. PATENT DOCUMENTS

| 3,421,766 | 1/1969 | Chimel et al. ................... 260/889 X |
| 3,572,721 | 3/1971 | Harrison et al. ................ 260/4 R X |
| 3,637,544 | 1/1972 | Lundberg et al. ............... 260/887 X |
| 3,652,720 | 3/1972 | Wright .............................. 525/186 X |
| 3,656,476 | 4/1972 | Swinney ................................ 128/90 |
| 3,692,023 | 9/1972 | Phillips et al. ....................... 128/90 |
| 3,764,639 | 10/1973 | Hsieh et al. ...................... 525/186 X |
| 3,919,163 | 11/1975 | Clendinning et al. ........... 525/186 X |
| 4,100,122 | 7/1978 | Kent .................................. 128/90 X |
| 4,141,559 | 2/1979 | Melvin et al. .................... 260/887 X |
| 4,141,863 | 2/1979 | Coran et al. ..................... 260/4 R X |
| 4,144,223 | 3/1979 | Kent .................................. 260/42.47 |

Primary Examiner—Lewis T. Jacobs
Attorney, Agent, or Firm—Stevens, Davis, Miller & Mosher

[57] ABSTRACT

Thermoplastic compositions are provided which comprise, as the polymeric materials, poly(epsilon caprolactone), a predominantly cis-1,4 polydiolefin and optionally an ionomer and, as filler, silica or calcium silicate. The compositions are useful in orthopaedic applications.

2 Claims, No Drawings

POLYMERIC CASTS

This invention is directed to novel compositions of matter, especially suitable as thermoplastic sheet material such as for orthopaedic use.

A number of polymeric materials are known which are thermoplastic in nature and are usable as orthopaedic materials and for the immobilization of fractured limbs. The most commonly known material for such uses is plaster of paris but more recently polymeric materials such as trans-1,4-polyisoprene, polychloroprene and poly(epsilon caprolactone) have been used. Sheet material containing trans-1,4-polyisoprene is in common use. Such polymeric materials have many advantages over plaster of paris including much greater ease of application, lighter weight and easy remoldability. Normally, such polymeric materials, compounded with small amounts of fillers, are supplied as sheets, which may or may not be perforated to better allow the dispersion of body fluids from under the cast, and are molded into shape by the simple technique of heating to a slightly elevated temperature. When warm, the sheet material is workable for a reasonable period of time allowing the final shaping of the splint or cast. It has generally been found that poly(epsilon caprolactone) shows a very short working time which tends to detract from its usefulness in orthopaedic applications.

These same polymeric materials may also be coated onto a fabric web, such as a bandage, and used as a bandage material which, on slight heating, can be unified into a strong cast-like form.

It has now been discovered that compositions comprising poly(epsilon caprolactone), a predominantly cis-1,4 polydiolefin and optionally an isomer are superior materials for use in orthopaedic applications, by which is meant the use of sheet, film or tape material to form a splint, cast, brace or support for immobilization or orthopaedic purposes on a human or animal body.

This invention is directed to novel compositions having thermoplastic properties comprising as the polymeric materials from about 70 to about 80 parts by weight of a poly(epsilon caprolactone), from about 5 to about 20 parts by weight of a predominantly cis-1,4 polydiolefin and from 0 to about 10 parts by weight of an ionomer, the total of such polymeric materials being 100 parts by weight, and as filler from about 10 to about 30 parts by weight, per 100 parts by weight of polymeric material, of a silica or calcium silicate.

Although poly(epsilon caprolactone) is known for use as a cast material, it was unexpected to find that the compositions of the present invention would be suitable for use in orthopaedic applications and would overcome the deficiencies of poly(epsilon caprolactone). Although poly(epsilon caprolactone) has a high modulus of elasticity and a high flexural strength, when compounded with a filler it tends to be inflexible and sheets of the polymer may crack or snap when bent through a large angle. The polymer loses its strength very rapidly at temperatures above about 50° C. and at 60° C. is quite soft, becoming very sticky at such temperatures. Additionally, the polymer shows a very short working time, the working time being that time for which the polymer is soft enough to be molded without being too soft and before it has hardened so as not to be workable. Similarly, if warmed to above about 50° C., the sheet material loses its strength rapidly and cannot even support its own weight. The predominantly cis-1,4 polydiolefins are rubbery materials and therefore have no thermoplastic properties. The ionomers are thermoplastic materials which generally show fairly high softening temperatures and therefore are not suitable for use in orthopaedic applications because the softening temperature is sufficiently high that it would cause severe discomfort for a patient being fitted with such a cast.

The poly(epsilon caprolactone) used in this invention is a polymer comprising predominantly cyclic ester monomer units of structure

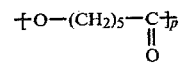

where p is not less than 100 and not more than about 3,000. The polymer is crystalline and has a relatively high strength, is generally white in appearance, has a melting point of about 60° C. and a reduced viscosity value of about 0.5 to about 10 as measured in benzene at 30° C., using a polymer concentration of 0.2 g polymer per 100 ml of benzene.

The predominantly cis-1,4 polydiolefin used in this invention is a polymer of a $C_4$ or $C_5$ conjugated diolefin, the cis-1,4 content of the polymer being at least about 80%, and preferably at least about 90%, of the double bonds in the polymer. Examples of suitable such polymers are cis-1,4-polybutadiene and both the natural and synthetic cis-1,4 polyisoprene. The cis-1,4 polybutadiene may be prepared using, for example, the various Ziegler catalyst. The cis-1,4-polyisoprene may be natural rubber or the synthetic material produced with the aid of the various Ziegler catalysts. These rubbers are well known in the art.

The ionomers are polymers of an unsaturated hydrocarbon and an unsaturated carboxylic acid which have been neutralized by reaction with an amine and/or an inorganic base. Typical ionomers are copolymers of ethylene and acrylic or methacrylic acid neutralized by reaction with mono- or di-valent metal ions, or a mixture thereof, such as sodium, lithium or calcium. Typically, the carboxylic acid content is from about 1 to about 7 mole percent of the copolymer. Ionomers are well known in the art, an example of a commercial product being SURLYN A (SURLYN is a Registered Trade Mark) from du Pont.

The filler used in the compositions of the present invention is silica or calcium silicate. The filler has an average particle size of from about 0.01 microns to about 0.25 microns and is normally a precipitated product. Preferably the filler has an average particle size of from about 0.01 to about 0.1 microns.

It was most unexpected that the polymer components used in the compositions of this invention would be sufficiently compatible to be mixed together without separating. It was also most unexpected to find that the compositions of this invention would, when mixed with the filler, have the balance of properties found.

The quantity of poly(epsilon caprolactone) used in the composition of the present invention is from about 70 to about 80 parts by weight. The amount of predominantly cis-1,4 polydiolefin used in the present compositions is from about 5 to about 20, preferably from about 10 to about 20, and most preferably from 15 to 20, parts by weight. The quantity of ionomer used is from 0 to about 10 parts by weight, preferably from 5 to 10 parts by weight. The total of the polymeric components is 100 parts by weight. The amount of filler in the present compositions is from about 10 to about 30, preferably from about 15 to about 25, parts by weight per 100 parts by weight of the polymeric components. The composition may also contain small amounts of other components, such as from about 0.5 to about 2 parts by weight per 100 parts by weight of polymeric components, of one or more polymer stabilizers for improved long term aging and one or more coloring agents, such as a pink color, for aesthetic reasons.

The compositions of the present invention are prepared using standard mixing procedures. The mixing may be on a rubber mill or in an internal mixer, operated at elevated temperatures of from about 200° to about 300° F. (about 93° to about 149° C.). When the mixing is complete, the mixture is cooled to about 100° to about 125° F. (about 38° to 52° C.) and sheeted off a mill to the desired thickness. If desired, it can be further molded at temperatures of about 250° to about 300° F. (about 121° to about 149° C.) for forming special size or shape sheets or for perforation of sheets. Sheet thickness may be from about 1 mm to about 7.5 mm. The sheet material may also be readily bonded to a fabric web, such as a bandage, by heating in contact with the fabric web.

The compositions of the invention exhibit a special balance of properties. The Shore C hardness is typically above about 70, preferably above about 75, up to about 90. The flexural strength of the compositions is above about 100 kg/cm$^2$, preferably above about 125 kg/cm$^2$. The flexural modulus of the compositions is generally above about 3,000, preferably above about 3,500 and most preferably, above about 4,000 kg/cm$^2$. When sheets of the present compositions are bent at room temperature, through about 180°, no cracking or breakage occurs. When warmed to about 60° C., such as by immersion in water at 60° C., sheets of the present compositions do not lose all their strength and will support their own weight without sagging, show good sheet to sheet adhesion and are easily moldable without being sticky. The warmed sheet molds easily for at least two to five minutes even while cooling down to ambient temperatures.

The following examples illustrate the present invention without limiting the scope thereof. All parts are parts by weight unless otherwise specified.

EXAMPLE

Compositions were prepared with the recipes shown in Table I. The poly(epsilon-caprolactone) used was supplied by Union Carbide under the designation PCL-700; the natural rubber was pale crepe; the trans-1,4 polyisoprene was supplied by Polysar Limited as TRANS-PIP (Registered Trade Mark); the polybutadiene was supplied by Polysar Limited as TAKTENE 1220 (TAKTENE is a Registered Trade Mark) and the silica was obtained from PPG as HiSil (Registered Trade Mark). The flexural strength and flexural modulus was determined according to the procedure ASTMD-790-66 Method A, on flexbars prepared according to ASTMD-618-61. The shore C Hardness was measured according to standard procedures.

Compositions 1 to 4 are controls outside the scope of the present invention. Compositions 5 to 12 are all within the scope of the present invention and show suitable strength and hardness characteristics and a good balance of properties at 60° C. showing their suitability for use in orthopaedic applications.

Casts were readily prepared from Compositions 5-12 by warming sheets of the compositions to 55°–60° C., by immersion in water or by warming in an oven, and wrapping the warmed sheets around a pencil as illustrative of a fractured joint and molding to the contours of the pencil. Adequate working time was available to mold and remold the material. On cooling, the casts hardened and developed rigidity such that they could not be broken without also breaking the enclosed pencil.

TABLE I

| | Composition No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Recipe | | | | | | | | | | | | |
| Poly(epsilon caprolactone) | 100 | 100 | — | — | 80 | 80 | 80 | 80 | 70 | 70 | 75 | 75 |
| Trans-1,4-polyisoprene | — | — | 100 | 100 | — | — | — | — | — | — | — | — |
| Natural rubber | — | — | — | — | 20 | 20 | 15 | 15 | 20 | 20 | — | — |
| Polybutadiene | — | — | — | — | — | — | — | — | — | — | 20 | 20 |
| Ionomer | — | — | — | — | — | — | 5 | 5 | 10 | 10 | 5 | 5 |
| Silica | 15 | 25 | 15 | 25 | 15 | 25 | 15 | 15 | 15 | 25 | 15 | 25 |
| Properties | | | | | | | | | | | | |
| Flexural strength kg/cm$^2$ | 298 | 247 | 154 | 129 | 133 | 142 | 129 | 147 | 104 | 128 | 112 | 129 |
| Flexural modulus kg/cm$^2$ | 7310 | 7560 | 3595 | 4030 | 3650 | 4550 | 3610 | 4835 | 2935 | 4945 | 3365 | 5100 |
| Hardness Shore C | 90 | — | 78 | — | 82 | — | 82 | — | 80 | — | 81 | — |
| Properties at 60° | | | | | | | | | | | | |
| Droop* | Poor | — | Ex. | — | Ex. | — | Ex. | — | Ex. | — | Ex. | — |
| Surface feel* | V.St. | — | Not | — | S.St. | — | Not | — | S.St. | — | Not | — |

*Ex. = excellent;
Not = not sticky;
V.St. = very sticky
S.St. = slightly sticky

What is claimed is:

1. A composition of matter having thermoplastic properties comprising 70 to 80 parts by weight of poly(epsilon caprolactone), 15 to 20 parts by weight of natural rubber or cis-1,4-polybutadiene having at least 80% cis-1,4 content, from 5 to 10 parts by weight of ionomer which is a copolymer of ethylene and acrylic or methacrylic acid neutralized by reaction with mono- or divalent metal ions (the total of these materials being 100 parts by weight), and 15 to 25 parts by weight of silica having an average particle size of from about 0.01 to 0.1 microns.

2. Compositions according to claim 1 in sheet form.

* * * * *